United States Patent
Wasmuth

(10) Patent No.: US 6,625,817 B2
(45) Date of Patent: Sep. 30, 2003

(54) TANNING BED CAP

(76) Inventor: Kimberly D. Wasmuth, 30 Arbour Crest Cir. NW., Calgary, Alberta (CA), T3G 4H1

( * ) Notice: Subject to any disclaimer, the term of this patent is extended or adjusted under 35 U.S.C. 154(b) by 0 days.

(21) Appl. No.: 10/083,820

(22) Filed: Feb. 27, 2002

(65) Prior Publication Data

US 2002/0116747 A1 Aug. 29, 2002

(51) Int. Cl.$^7$ ................................................ A42B 1/04
(52) U.S. Cl. .................................................... 2/174
(58) Field of Search ........................... 2/410, 455, 468, 2/171, 171.8, 172, 174, 175.1, 175.6, 181, 200.1, 7, 8, 68, 171.03, 906, 918

(56) References Cited

U.S. PATENT DOCUMENTS

| | | | | |
|---|---|---|---|---|
| 2,357,851 A | * | 9/1944 | Scheyer | 442/131 |
| 2,726,398 A | * | 12/1955 | Cooper | 2/68 |
| 3,327,720 A | * | 6/1967 | Carmony et al. | 132/274 |
| 3,746,015 A | * | 7/1973 | Schulman | 132/212 |
| 3,766,565 A | * | 10/1973 | Cozzens | 2/209.7 |
| 4,542,595 A | * | 9/1985 | Shon | 34/95 |
| 4,683,596 A | * | 8/1987 | Cole | 2/174 |
| 4,887,319 A | * | 12/1989 | Daniels | 2/410 |
| 5,323,491 A | * | 6/1994 | Barrett, Jr. | 2/172 |
| 5,477,561 A | * | 12/1995 | Adkins | 2/174 |
| 5,603,120 A | * | 2/1997 | Gifford | 2/172 |
| 6,061,836 A | * | 5/2000 | Peters | 2/175.6 |
| 6,216,278 B1 | * | 4/2001 | Nguyen et al. | 2/174 |

* cited by examiner

Primary Examiner—Gary L. Welch

(57) ABSTRACT

A tanning bed cap includes a pliant body having at least one layer, an interior cavity and a head receiving opening providing access to the interior cavity. The layer is either one of an insulating material, a reflective material or both. The head receiving opening has a peripheral elastic, whereby the head receiving opening engages a head of a person wearing the cap. The tanning bed cap protects ones hair from ultraviolet radiation.

7 Claims, 2 Drawing Sheets

TANNING BED CAP

FIELD OF THE INVENTION

The present invention relates to a cap that is intended for use by persons using tanning beds.

BACKGROUND OF THE INVENTION

Tanning salons have become popular with persons wishing to tan their skin to enhance their appearance, but who either do not live in a climate that permits sun tanning all year round or live a lifestyle that does not permit the time for regular sun tanning.

The heat and ultraviolet rays generated by tanning beds used in the tanning salons are known to cause damage to ones hair. Patrons are, therefore, forced to take remedial steps to revive damaged hair by using specially formulated shampoos and conditioners.

SUMMARY OF THE INVENTION

What is required is a cap that is suitable for use in a tanning bed to protect ones hair.

According to the present invention there is provided a tanning bed cap which includes a pliant body having at least one layer, an interior cavity and a head receiving opening providing access to the interior cavity. The at least one layer is either one of an insulating material or a reflective material. The head receiving opening has a peripheral elastic, whereby the head receiving opening engages a head of a person wearing the cap.

Wearing a cap usually retains heat around the head. This causes patrons to perspire heavily and messes their hair. For persons sufficiently concerned about their appearance to want to indulge in tanning, this disadvantage will normally outweigh any advantage to be gained in protecting one's hair from damage through the use of a cap. The sun tanning cap, as described above, reduces the extent to which patrons will perspire when wearing the cap, through the use of a reflective layer, an insulating layer or both. A reflective layer reflects ultraviolet rays to reduce heat within the interior cavity. An insulating layer thermally isolates the interior cavity.

BRIEF DESCRIPTION OF THE DRAWINGS

These and other features of the invention will become more apparent from the following description in which reference is made to the appended drawings, the drawings are for the purpose of illustration only and are not intended to in any way limit the scope of the invention to the particular embodiment or embodiments shown, wherein.

DETAILED DESCRIPTION OF THE PREFERRED EMBODIMENT

Figure 1:
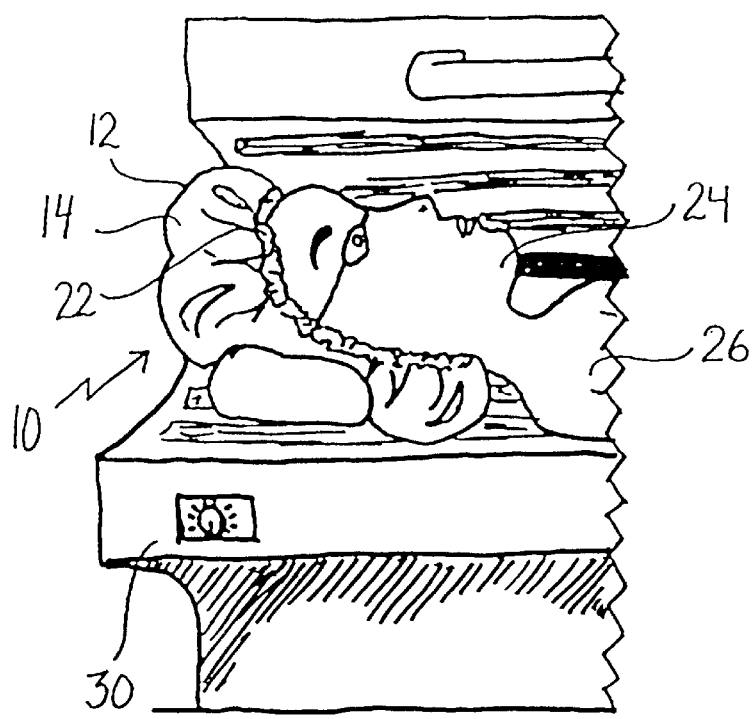
FIG. 1 is a perspective view of a tanning bed cap constructed in accordance with the teachings of the present invention in use by a person tanning in a tanning bed.

The preferred embodiment, a tanning bed cap generally identified by reference numeral 10, will now be described with reference to FIGS. 1 through 4.

Structure and Relationship of Parts

Figure 2:
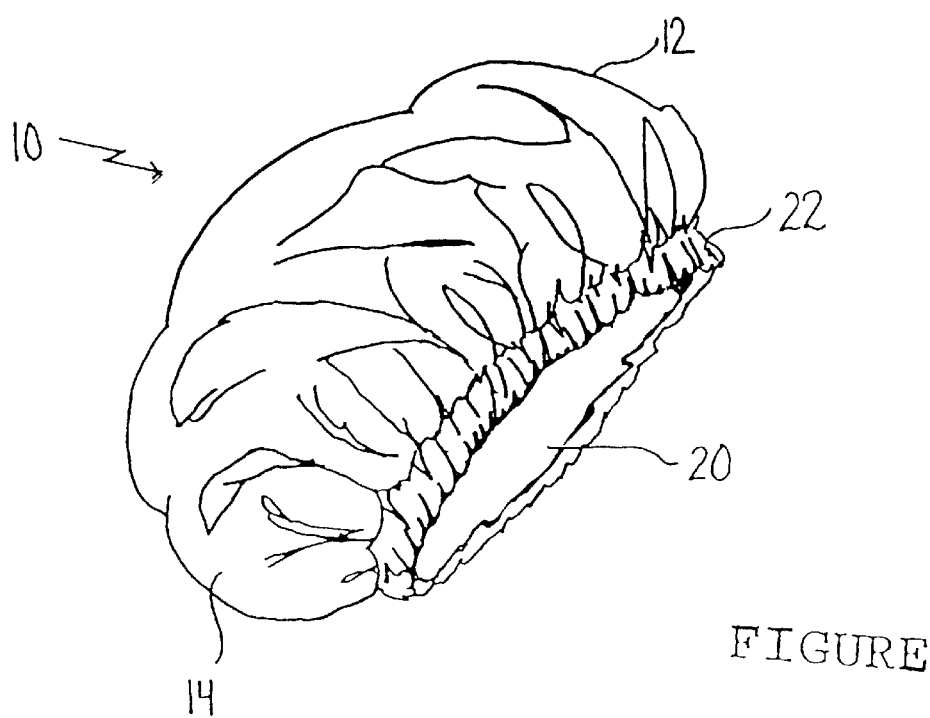
FIG. 2 is a perspective view of the tanning bed cap illustrated in FIG. 1.
Figure 3:
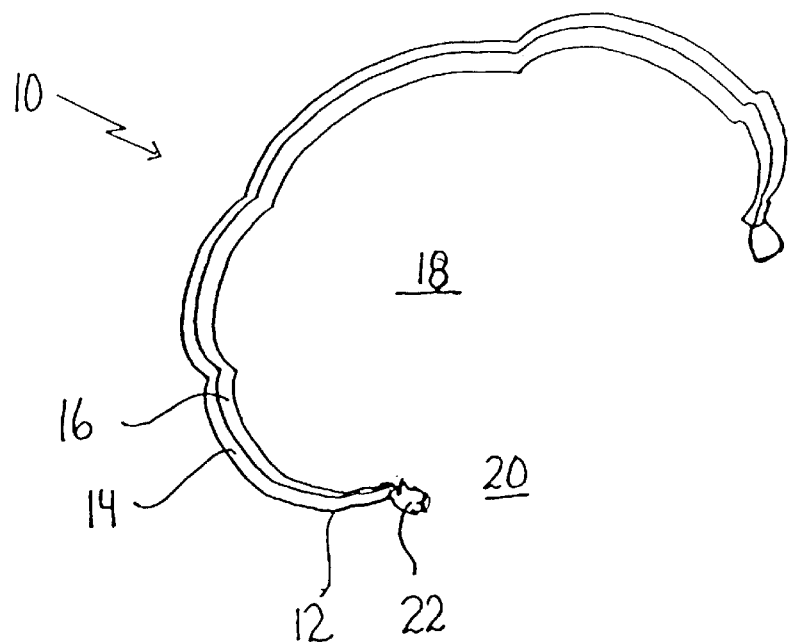
FIG. 3 is a section view of the tanning bed cap illustrated in FIG. 2.
Figure 4:
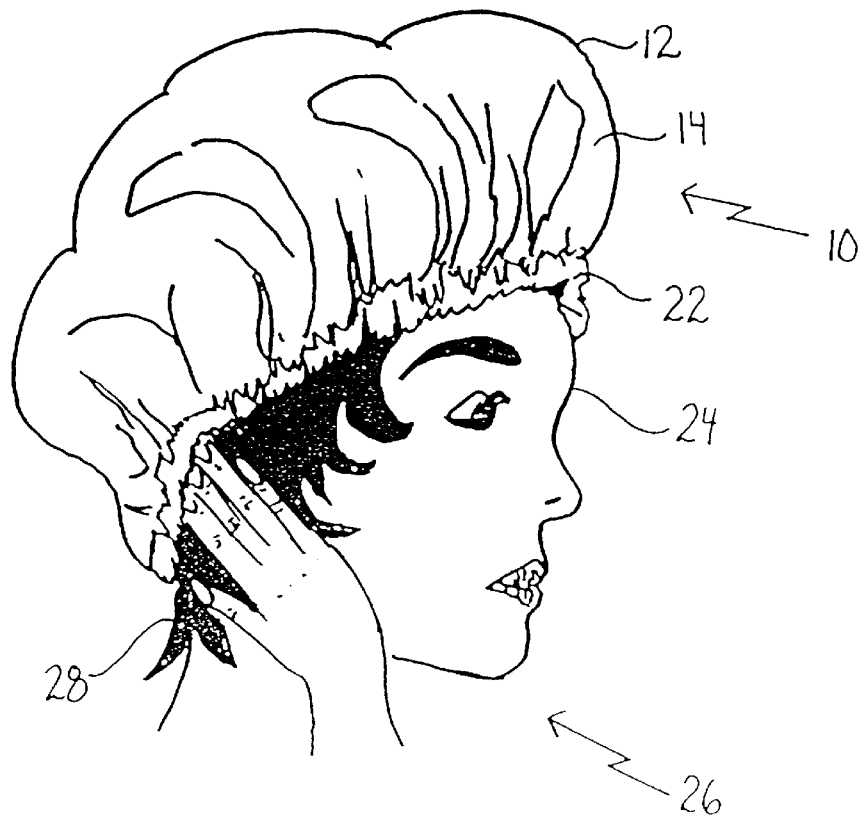
FIG. 4 is a side elevation view of the tanning bed cap illustrated in FIG. 2, being placed onto a person's head.

Referring to FIG. 3, there is provided a tanning bed cap 10 that includes a pliant layered body 12 having an outer layer 14, an inner layer 16, an interior cavity 18 and a head receiving opening 20 which provides access to interior cavity 18. Outer layer 14 is of a reflective material, thereby reflecting ultraviolet rays. Inner layer 16 is of an insulating material, thereby reducing heat build up within interior cavity 18. Referring to FIG. 2, head receiving opening 20 has a peripheral elastic 22. Referring to FIG. 4, head receiving opening 20 engages a head 24 of a person 26 wearing tanning cap 10.

Operation

The use of tanning cap 10 will now be described with reference to FIGS. 1 through 4. Referring to FIG. 1, tanning cap 10 is intended for use by a person 26 using a tanning bed 30. Referring to FIG. 4, prior to entering tanning bed 30, person 26 places tanning cap 10 over their hair 28 by inserting their head 24 through head receiving opening 20. Peripheral elastic 22 will secure tanning cap 10 in place on head 24. If any hair 28 extends outside tanning cap 10, person 26 can tuck hair 28 up under peripheral elastic 22 so that tanning cap 10 covers and contains all of hair 28 within interior cavity 18 so that no hair 28 is left exposed. Referring to FIG. 1, once tanning cap 10 is securely in place with all hair 28 covered, person 26 can use tanning bed 30 as they normally would. Peripheral elastic 22 prevents hair 28 from escaping from tanning cap 10. Tanning cap 10 completely covers hair 28. Reflective outer layer 14 shields the hair from ultra-violet radiation. Insulating inner layer 16 reduces heat build-up within interior cavity 18 and thereby reduces perspiration which would otherwise have a detrimental effect on the hairdo of person 26. It is preferred that both outer layer 14 and inner layer 16 are made of a breathable material. This helps prevent the kind of heat build up that occurs with plastic shower caps, that not only do not prevent heat build up but actually promote it. One material that has been found to be satisfactory is polyester.

Supporting Data

In order to develop empirical data regarding the effectiveness of a tanning bed cap fabricated in accordance with the teachings of the present invention as compared to white terry cloth towels presently given to patrons of tanning studios a series of tests were conducted. These tests were conducted by the Textile Testing Service at the University of Nebraska at Lincoln. The mean ultraviolet protection factor (UPF) rating assigned the tanning bed cap after the tests was 1000.00. The mean UPF rating assigned the white terry cloth towel after the tests was, by comparison, 15.29. The white terry cloth towel is giving virtually no ultraviolet protection to the sun tanning studio patron.

In this patent document, the word "comprising" is used in its non-limiting sense to mean that items following the word are included, but items not specifically mentioned are not excluded. A reference to an element by the indefinite article all does not exclude the possibility that more than one of the element is present, unless the context clearly requires that there be one and only one of the elements.

It will be apparent to one skilled in the art that modifications may be made to the illustrated embodiment without departing from the spirit and scope of the invention as hereinafter defined in the Claims.

The embodiments of the invention in which an exclusive property or privilege is claimed are defined as follows:

1. A tanning bed cap comprising:
   a pliant layered body having an outer layer and an inner layer, the pliant layered body defining an interior cavity and having a head receiving opening which provides access to the interior cavity;

the outer layer being of a reflective material and having a sufficiently high UltraViolet Protection Factor rating to reflect ultraviolet rays;

the inner layer being of a insulating material for reducing heat build up within the interior cavity during use;

the head receiving opening having a peripheral elastic, whereby the head receiving opening engages a head of a person wearing the cap; and the sufficiently high UltraViolet Protection Factor rating is about 1000.

2. The tanning bed cap as defined in claim 1, wherein both the outer layer and the inner layer are of a breathable material, thereby permitting heat to escape from the interior cavity through the inner layer and the outer layer without any non-breathable intermediate layer between the inner and outer layers to impede the escape of heat.

3. The tanning bed cap as defined in claim 1, wherein both the outer layer and the inner layer are of a breathable material, thereby permitting heat to escape from the interior cavity through the inner layer and the outer layer without any non-breathable intermediate layer between the inner and outer layers to impede the escape of heat;

the outer layer and the inner layer directly contact one another.

4. A tanning bed cap comprising:

a pliant layered body consisting only of an outer layer and an inner layer without any layer between the outer layer and the inner layer, and the pliant layered body defining an interior cavity and having a head receiving opening which provides access to the interior cavity;

the outer layer being of a reflective material and having a sufficiently high UltraViolet Protection Factor rating to reflect ultraviolet rays;

the inner layer being of a insulating material for reducing heat build up within the interior cavity during use, and the outer layer contacting the inner layer;

the head receiving opening having a peripheral elastic, whereby the head receiving opening engages a head of a person wearing the cap; and the sufficiently high UltraViolet Protection Factor rating is about 1000.

5. The tanning bed cap as defined in claim 4, wherein both the outer layer and the inner layer are of a breathable material, thereby permitting heat to escape from the interior cavity through the inner layer and the outer layer without any non-breathable intermediate layer between the inner and outer layers to impede the escape of heat.

6. The tanning bed cap as defined in claim 4, wherein the outer layer and the inner layer directly contact one another.

7. The tanning bed cap as defined in claim 4, wherein both the outer layer and the inner layer are of a breathable material, thereby permitting heat to escape from the interior cavity through the inner layer and the outer layer without any non-breathable intermediate layer between the inner and outer layers to impede the escape of heat;

the sufficiently high UltraViolet Protection Factor rating is about 1000; and the outer layer and the inner layer directly contact one another.

* * * * *